(12) United States Patent
Goldstein et al.

(10) Patent No.: US 8,678,011 B2
(45) Date of Patent: Mar. 25, 2014

(54) EXPANDABLE EARPIECE SEALING DEVICES AND METHODS

(75) Inventors: Steven Wayne Goldstein, Delray Beach, FL (US); John Patrick Keady, Boca Raton, FL (US)

(73) Assignee: Personics Holdings, Inc., Boca Raton, FL (US)

( * ) Notice: Subject to any disclaimer, the term of this patent is extended or adjusted under 35 U.S.C. 154(b) by 1166 days.

(21) Appl. No.: 12/172,834

(22) Filed: Jul. 14, 2008

(65) Prior Publication Data

US 2009/0022353 A1    Jan. 22, 2009

Related U.S. Application Data

(60) Provisional application No. 60/949,398, filed on Jul. 12, 2007.

(51) Int. Cl.
*A61F 11/00*    (2006.01)

(52) U.S. Cl.
USPC .......................................... 128/864; 181/135

(58) Field of Classification Search
USPC ........... 128/864–865, 867–868; 181/130, 135
See application file for complete search history.

(56) References Cited

U.S. PATENT DOCUMENTS

| | | | |
|---|---|---|---|
| 2,535,258 A | 12/1950 | Bland | |
| 2,876,767 A * | 3/1959 | Wasserman | 128/865 |
| 3,602,654 A | 8/1971 | Victoreen | |
| 4,133,984 A * | 1/1979 | Akiyama | 381/328 |
| 4,539,440 A * | 9/1985 | Sciarra | 381/329 |
| 4,741,344 A | 5/1988 | Danby et al. | |
| 4,834,211 A | 5/1989 | Bibby et al. | |
| 4,896,679 A | 1/1990 | St. Pierre | |
| 4,962,537 A | 10/1990 | Basel et al. | |
| 5,033,090 A * | 7/1991 | Weinrich | 381/318 |
| 5,333,622 A | 8/1994 | Casali et al. | |
| 5,483,027 A | 1/1996 | Krause | |
| 6,094,494 A | 7/2000 | Haroldson | |
| 6,256,396 B1 | 7/2001 | Cushman | |
| 6,339,648 B1 | 1/2002 | McIntosh et al. | |
| 6,393,130 B1 | 5/2002 | Stonikas et al. | |
| 6,513,621 B1 * | 2/2003 | Deslauriers et al. | 181/130 |
| 6,671,381 B1 | 12/2003 | Lux-Wellenhof | |
| 7,130,437 B2 | 10/2006 | Stonikas et al. | |
| 7,164,775 B2 | 1/2007 | Meyer et al. | |
| 7,227,968 B2 | 6/2007 | van Halteren et al. | |
| 7,362,875 B2 | 4/2008 | Saxton et al. | |
| 7,387,187 B2 | 6/2008 | Widmer et al. | |
| 2004/0258263 A1 * | 12/2004 | Saxton et al. | 381/328 |
| 2005/0094835 A1 * | 5/2005 | Doty | 381/328 |
| 2006/0159298 A1 | 7/2006 | von Dombrowski et al. | |
| 2007/0116319 A1 | 5/2007 | Hagberg | |
| 2008/0144871 A1 | 6/2008 | Purcell et al. | |
| 2009/0173353 A1 | 7/2009 | Purcell et al. | |
| 2009/0320858 A1 | 12/2009 | Purcell et al. | |
| 2009/0320859 A1 | 12/2009 | Purcell et al. | |

* cited by examiner

*Primary Examiner* — Allen Parker

(57) ABSTRACT

Orifice insertion devices are provided. An orifice insertion device includes a stent and a plurality of sealing elements. Each sealing element is attached to the stent. At least one sealing element includes an expandable section configured to exert a pressure on an ear canal wall to seal an ear canal, without appreciable deformation of the ear canal wall. At least two of the plurality of sealing elements are formed from different materials.

11 Claims, 3 Drawing Sheets

EXPANDABLE EARPIECE SEALING DEVICES AND METHODS

CROSS REFERENCE TO RELATED APPLICATIONS

This Application is a Non-Provisional and claims the priority benefit of Provisional Application No. 60/949,398 filed on 12 Jul. 2007, the entire disclosure of which is incorporated herein by reference.

FIELD OF THE INVENTION

The invention relates in general to devices and methods of earphone, earpiece, earbud, fit and sealing technology, and particularly though not exclusively, is related to expandable sealing mechanisms for earpieces.

BACKGROUND OF THE INVENTION

Present day ear devices are intended to deliver information to the ear via off-the-shelf or custom-molded pieces that present the information primarily in the outer third of the ear canal, often with questionable attention to the actual fit, comfort, and consideration of the ear anatomy and physiology.

Current systems do not use inflatable or expandable systems to achieve sound isolation and sealing.

SUMMARY OF THE INVENTION

At least one exemplary embodiment is related to an earpiece (e.g., earphone, earbud, or other devices configured to direct acoustic signals to the ear) inserted into the ear canal, where a portion of a sealant section acoustically seals a medial portion of the external auditory canal.

At least one exemplary embodiment is directed to an earpiece that includes: a sealing section, where the sealing section includes an expandable bladder; an ambient sound microphone (ASM); an ear canal receiver (ECR); an ear canal microphone (ECM); a wireless communication module; a power source; and a logic circuit.

Further areas of applicability of embodiments of the present invention will become apparent from the detailed description provided hereinafter. It should be understood that the detailed description and specific examples, while indicating exemplary embodiments of the invention, are intended for purposes of illustration only and are not intended to limit the scope of the invention.

BRIEF DESCRIPTION OF THE DRAWINGS

Exemplary embodiments of the present invention will become apparent from the following detailed description taken in conjunction with the following drawings, wherein.

DETAILED DESCRIPTION

Figure 1:
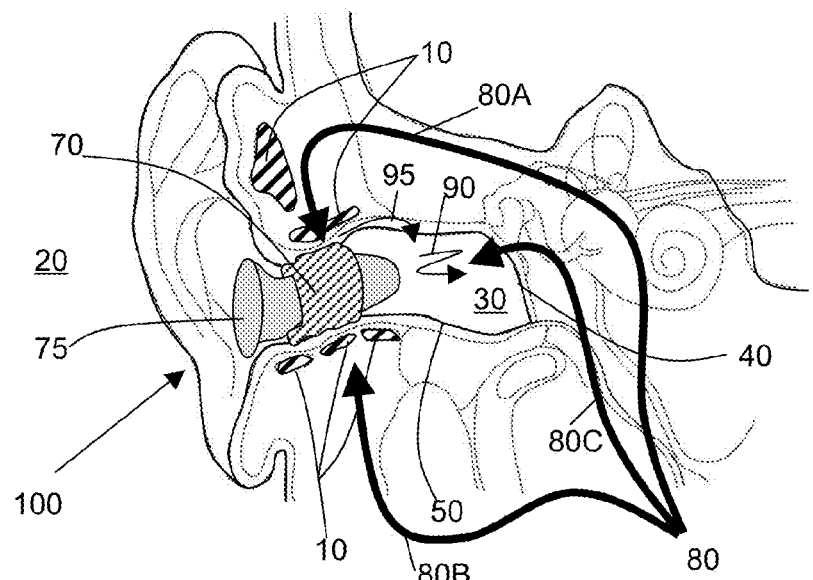
FIG. 1 illustrates an ear canal as a non-limiting example of an orifice that can be sealed with an earpiece according to at least one exemplary embodiment.

The following description of exemplary embodiment(s) is merely illustrative in nature and is in no way intended to limit the invention, its application, or uses.

Exemplary embodiments are directed to or can be operatively used on various wired or wireless earpiece devices (e.g., earbuds, headphones, ear terminals, hearing aids, behind the ear devices, or other acoustic devices as known by one of ordinary skill in the art, and equivalents).

Processes, techniques, apparatus, and materials as known by one of ordinary skill in the art may not be discussed in detail but are intended to be part of the enabling description where appropriate. For example material fabrication may not be disclosed, nor attachment procedures (e.g., adhesive attaching of separate ridge structures), but such, as known by one of ordinary skill in such arts is intended to be included in the discussion herein when necessary.

Notice that similar reference numerals and letters refer to similar items in the following figures, and thus once an item is defined in one figure, it may not be discussed or further defined in the following figures.

FIG. 1 illustrates a sealed (occluded) ear canal 50, with a sealed volume 30 (sealed from receiving sound from ambient environment 20). Voice can leak 80 into the sealed volume 30 between insertion element 75 and eardrum 40 from various source paths 80A, 80B, and 80C. Source paths 80A and 80B represent sound conducted from bones 10 adjacent to ear canal 50. Source path 80C represents sounds 90, 95 to ear canal 50 from other areas of the ear. In one explanation, the leaked acoustic energy results in an amplification (e.g., by resonance) at certain frequencies within the sealed volume, resulting in the occlusion effect. If the ear canal 50 (a non-limiting example of an orifice) was unsealed then no resonance could build and hence there would be no occlusion effect. While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments.

FIG. 1 illustrates at least one exemplary embodiment. An earpiece 100 can include an insertion element 75 operatively connected to a sealing section. The sealing section can include an expandable section 70 (e.g., expanding polymers, inflatable systems, mechanically expanded systems).

The expandable section 70 can be inflatable (e.g., fluid (gas or liquid)) of deformable fillable material. For example the fillable material referred to herein can be viscous and can include silicone-based polymers, gels, vinyl elastomers, or any other material of sufficient properties to allow the deformation of a membrane cavity from user contact. Materials can also be used to provide a slow reformation of the original membrane cavity shape after it has been deformed and released. In this regard, a silicone gel or other non-cross-linked polymer or uncatalyzed materials may be used. It should be appreciated that the composition of the fillable material could be altered for applications in which varied membrane characteristics are desired (i.e. more stiffness, durability, more or less deformability and/or longer-lasting deformation). The fillable material may be elastically deformed or it may be deformed by displacement, which is the actual movement or flow of the fillable material in response to pressure, such as that from a user's fingertips. In addition, the fillable material could be altered for applications in which varied temperature or light conditions would be encountered during the use of particular products on which the membrane cavity is mounted.

The portion of a membrane connected to a structure (base membrane) can be made of any material, rigid or elastic, including various plastic or metal materials, or it can be made of a membrane formed of thin rubber-based material, deformable plastic or silicone-based materials or other elastomeric materials suitable for a given application. If the base is configured as a flexible membrane, the cavity can more easily conform to a product's surface, thereby increasing the ease with which the cavity can be installed, removed, and replaced. Likewise, the outer membrane also can be made of a thin rubber-based material, deformable plastic or silicone polymer materials, or other elastomeric materials suitable for a given application. If the base membrane and outer membrane are made of silicone material, both should be from 0.50 mm to 2.5 mm in thickness. In this regard, the base may be a membrane instead of a piece of rigid material. The edges of the outer membrane and the base membrane can be mechanically fastened or clamped forming the membrane cavity. Additionally, at least a portion of the base membrane can be adhesively attached (e.g., adhesive tape, glue) or mechanically fastened to the support structure.

The silicone sealant can be of an acetoxy cure type. In particular, upon exposure to moisture, the silicone sealant will give off small amounts of acetic acid while the sealant cures. It is not recommended that the acetic acid vapors be inhaled. The sealant will cure in 24 hours and has a tack free time of 10-20 minutes at 77.degree. F. (25.degree. C.) with 50% relative humidity. The sealant's tensile strength is approximately 350 psi, its elongation property is 450%, and its hardness is approximately 25-30 Shore A. The sealant has temperature stability from −85.degree. F. to 450.degree. F. (−65.degree. C. to 232.degree. C.) and can withstand intermittent exposure to temperatures as high as 500.degree. F. (280.degree. C.). The sealant is believed to have good resistance to various weathering conditions, including UV radiation, rain, snow, etc, without hardening, cracking, or shrinking.

For optimum adhesion with the above adhesive, the support structure and the lower surface of the base membrane should be clean, dry, and free from oil, grease or other foreign material. If necessary, metal surfaces should be wiped with a non-oily solvent. Rubber surfaces should be abraded to promote adhesion. Depending on environmental conditions, the base and product surface should be joined within 5-10 minutes, before the tack-free time of the sealant passes.

If the expandable section 70 includes a fluid (gas or liquid) the fluid can be variable for example $H_2$, $O_2$, air, and water, where the membrane can be designed to vary porosity to the fluid leakage through the membrane. For example for some gases (e.g., $H_2$) the wall thickness can be increased (e.g., 3 times that of air) to decrease the porosity of $H_2$ through an inflatable membrane.

Typical dimensions of the expandable section include a fully expanded dimension that is slightly larger than the orifice (e.g., nose, throat, vein, anal, ear canal) opening.

Figure 2:
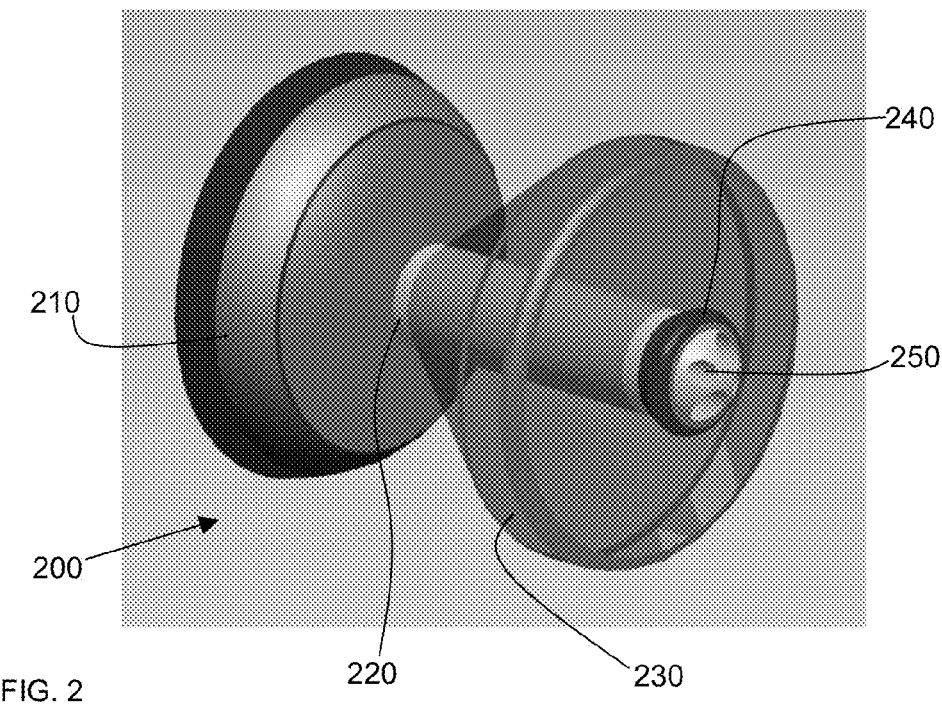
FIG. 2 illustrates an orifice insertion device according to at least one embodiment.

FIG. 2 illustrates an orifice insertion device 200, that has an optional stop flange 210. The stop flange 210 can be designed to stop at the opening of an orifice. The stop flange 210 can be attached to a stent 220 (e.g., multilumen tube, single lumen tube) that can vary in durometer (e.g., 25-80 urethane, steel, wood). As illustrated in FIG. 2 the stent 220 is a multi-lumen tube with various openings (e.g., 250). An expandable section 230 can be operatively attached to the stent 220 (e.g., heat bonded, shrink wrapped, glued). Optionally a guide section 240 (e.g., soft foam tip, additional inflatable system) can be attached near the end of the stent 220 to aid in the insertion of the orifice device 200 (e.g., earpiece).

Figures 3, 4:
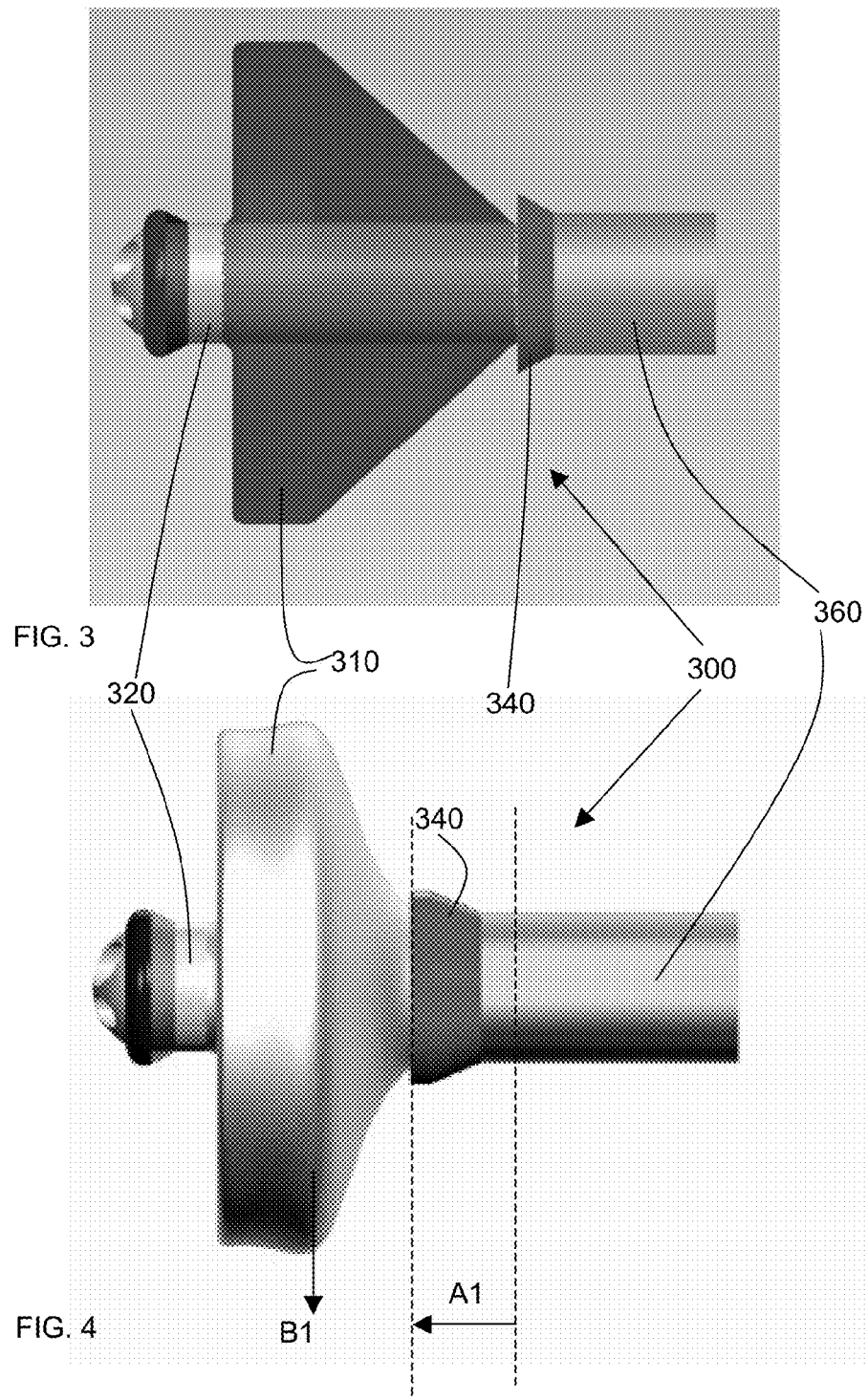
FIGS. 3 and 4 illustrate a stent used to inflate an expandable section of the device.
Figure 6:
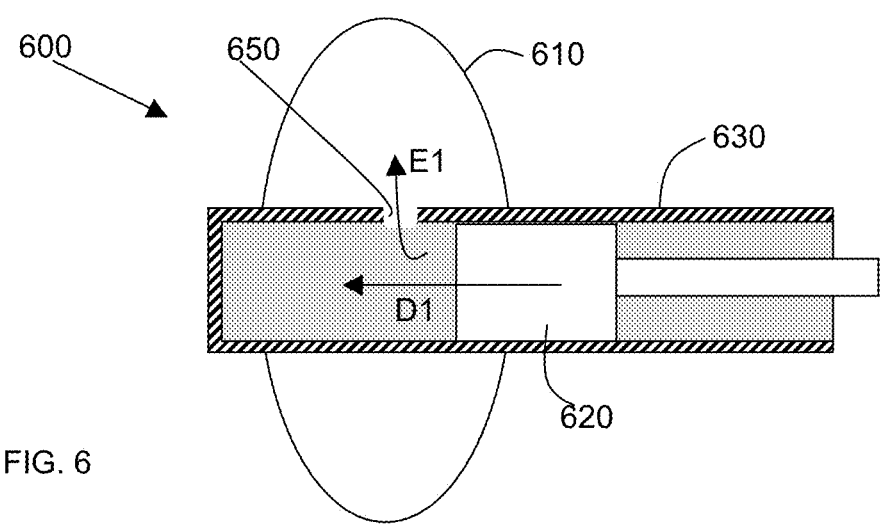
FIG. 6 illustrates an internal piston mechanism that can be used to increase the pressure in the inflatable membrane on a stent.

In an embodiment, the expandable section 230 of the earpiece is an inflatable device. Several methods can be used to inflate the expandable section 230. For example FIGS. 3 and 4 illustrate an orifice insertion device 300 including a stent 320, operatively connected to an inflatable membrane 310 (e.g., balloon), where a push mechanism (340 and 360) moves along the stent 320 in direction A1, to compress the inflatable membrane 310 along direction B1. Additionally FIG. 6 illustrates an orifice insertion device 600 including an internal piston mechanism 620 that can be used (e.g., moved along direction D1) to increase the pressure E1 in the inflatable membrane 610 on a stent 630 (via opening 650 in stent 630).

Figure 5:
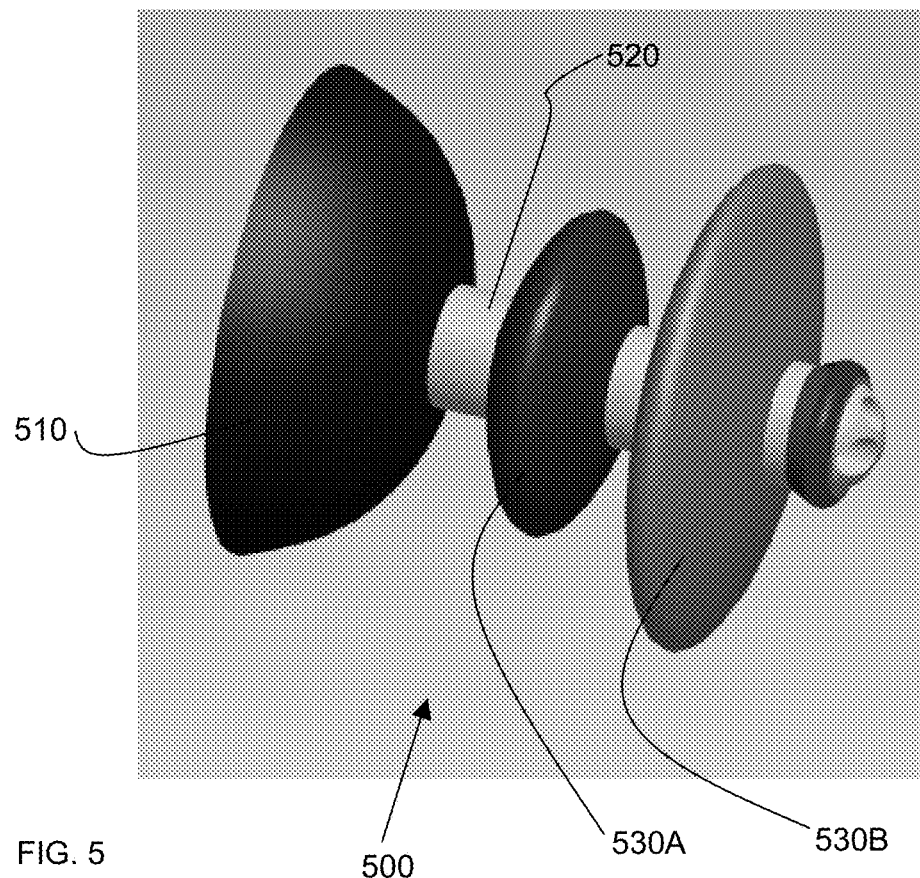
FIG. 5 illustrates a multiple expandable system where various combinations of expandable systems can be combined on a stent.

FIG. 5 illustrates a multiple expandable system where various combinations of expandable systems (e.g., one inflatable the other foam), can be combined on a stent 520. The orifice insertion device 500 illustrated in FIG. 5 shows two expandable section 530A and 530B. The orifice insertion device 500 also illustrates stop flange 510. Both can be expanded by methods discussed previously and at different times. For example expandable section 530A can be inflated (if it were an inflatable system) if a trigger event (e.g., excess sound pressure level (e.g., 100 dB)) were reached.

In the examples illustrated above the sealing sections have been illustrated as homogeneous material, which in some cases can expand in response to thermal variations. Additional exemplary embodiments can include expandable sections, that can include temperature expanding materials varying in a sandwich type configuration, and/or an expandable membrane or bladder that is expanded to touch and press against the ear canal wall to provide sealing. In addition to varying penetration into the depths of the ear canal for various devices, at least one exemplary embodiment includes an earpiece device that seals near the concha or the external auditory meatus. For example the earpiece device can have a concha support piece to which is attached to an ear terminal (portion penetrating into the ear canal), where the ear terminal seals and seats near the external auditory meatus.

In at least one exemplary embodiment the compression can be driven by a piston, where the piston can be driven by a linear actuator or via a pneumatic system where an incompressible fluid presses against one side of the piston forcing it in a direction compressing the bladder.

Additional exemplary embodiments can use an expandable bladder as a sealing section where one side of an inner wall moves as driven by actuators, gears, pneumatics or other methods as one of ordinary skill would know, and presses on the bladder expanding the bladder into the ear canal. The bladder can be attached to the moveable wall so that retraction of the wall retracts the bladder from the ear canal.

At least one exemplary embodiment is directed to an orifice insertion device comprising: a stent; and a sealing element where the sealing element is operatively attached to the stent, wherein the sealing element includes at least a first expandable section, where the expandable section is configured to exert a pressure on an orifice wall sufficient to seal the orifice without appreciable deformation of the orifice wall. The pressure exerted can vary depending upon the orifice wall's material composition and rigidity. For example in flesh the pressure exerted can lie between 1 atmospheres and 5 atmospheres, where an atmosphere is the pressure at sea level.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An orifice insertion device configured to be inserted into an ear canal, the orifice insertion device comprising:
   a stent; and
   a plurality of sealing elements where each sealing element is operatively attached to the stent, wherein two sealing elements of the plurality of sealing elements include an expandable section configured to be disposed within the ear canal and to exert a pressure on an ear canal wall sufficient to seal the ear canal without appreciable deformation of the ear canal wall,
   wherein the two sealing elements are formed from different materials, and
   wherein a further one of the plurality of sealing elements is configured to seal an opening of the ear canal.

2. The orifice insertion device according to claim 1, where the pressure is between about 1 atmosphere at sea level and about 3 atmospheres at sea level.

3. The orifice insertion device according to claim 1, where the pressure is greater than about 1 atmosphere at sea level and less than about 1.75 atmospheres at sea level.

4. The orifice insertion device according to claim 1, where the expandable section of at least one of the two sealing elements includes a membrane that expands to press against a portion of the ear canal wall.

5. The orifice insertion device according to claim 4, where the membrane is a bladder and contains a fluid.

6. The orifice insertion device according to claim 5, where the fluid is a gas.

7. The orifice insertion device according to claim 4, where the membrane expands in a first direction in response to an applied pressure in a second direction.

8. The orifice insertion device according to claim 7, further including a pneumatic fluid piston system coupled to the membrane and configured to provide the applied pressure.

9. The orifice insertion device according to claim 7, further including a mechanical element coupled to the membrane and configured to provide the applied pressure.

10. The orifice insertion device according to claim 9, where the mechanical element is locked when the expandable section is expanded.

11. The orifice insertion device according to claim 1, where:
   a first expandable section of one of the two sealing elements includes a membrane containing a fluid, the membrane configured to expand to press against a portion of the ear canal wall, and
   a second expandable section of a remaining one of the two sealing elements includes a foam material that is elastically deformed to press against a further portion of the ear canal wall.

* * * * *